(12) United States Patent
Wächtler et al.

(10) Patent No.: US 6,353,125 B1
(45) Date of Patent: Mar. 5, 2002

(54) PERFLUORO-N-ALKYLSULFONIC ACID DERIVATIVES

(75) Inventors: Andreas Wächtler, Tübingen; Karl-Heinz Derwenskus, Darmstadt; Andreas Meudt, Frankfurt, all of (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/600,295

(22) PCT Filed: Jan. 11, 1999

(86) PCT No.: PCT/EP99/00119

§ 371 Date: Sep. 25, 2000

§ 102(e) Date: Sep. 25, 2000

(87) PCT Pub. No.: WO99/36397

PCT Pub. Date: Jul. 22, 1999

(30) Foreign Application Priority Data

Jan. 15, 1998 (DE) .......................................... 198 01 248

(51) Int. Cl.[7] .................... C07C 303/00; C07C 305/00; C07F 9/50
(52) U.S. Cl. .............................. 558/54; 568/8; 568/17
(58) Field of Search .............................. 558/44, 53, 54; 568/8, 17

(56) References Cited

U.S. PATENT DOCUMENTS 3,346,612 A * 10/1967 Hansen
5,399,771 A    3/1995 Cai et al.

OTHER PUBLICATIONS

CA:132:64403 abs of JP 2000007690 Jan. 11, 2000.*
CA:78:1242000 abs of Justus Liebigs Ann. Chem. by Niederpruem et al (1) pp 20–32 1973.*
CA:124:320156 abs of Akita Kogyo Koto Senmon Gakko Kenkyu Kiyo by Tsuruta, M 31, pp 74–7 1996.*

* cited by examiner

Primary Examiner—Jean F. Vollano
(74) Attorney, Agent, or Firm—Millen, White, Zelano & Branigan, P.C.

(57) ABSTRACT

Described are bis(perfluoro-n-alkane-sulfonate) compounds, methods for preparing these compounds and use of these compounds, for example as starting materials for the synthesis of chiral and phosphine ligands for transition metal catalysts.

17 Claims, No Drawings

PERFLUORO-N-ALKYLSULFONIC ACID DERIVATIVES

This is the national stage of PCT/EP99/00119, filed Jan. 11, 1999, now WO 9936397.

The invention relates to novel bis(perfluoro-n-alkanesulfonates) of the formula I:

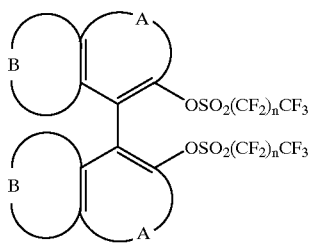

where
n is 3, 4, 5, 6, 7, 8 or 9,

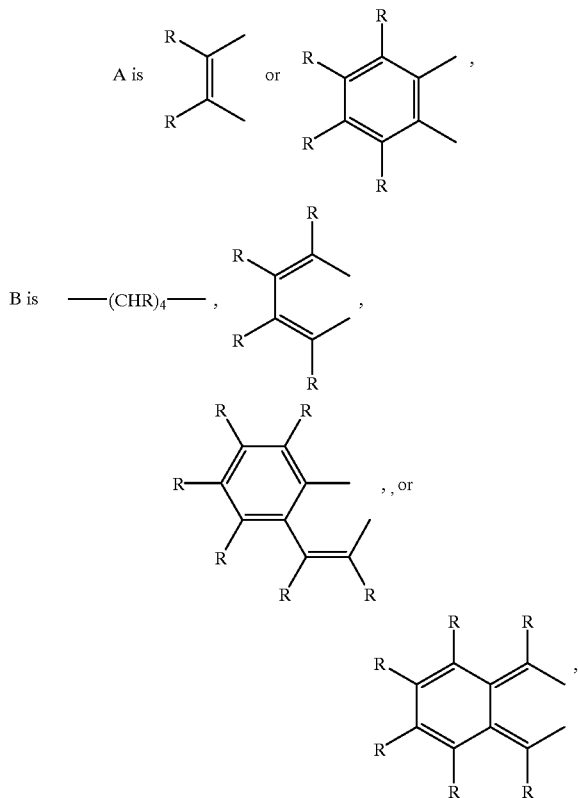

where nonadjacent groups =CR— may be replaced by =N—, and —CHR— may be replaced by —NR—, —O— or —S— and R is alkyl or alkoxy having from 1 to 12 carbon atoms, halogen, —CN, —CF$_3$, —OCF$_3$ or unsubstituted phenyl or phenyl which is monosubstituted or polysubstituted by alkyl or alkoxy having from 1 to 12 carbon atoms, halogen or —CN, where if more than one R is present the substituents R may be identical or different.

The invention also relates to a process for preparing the bis(perfluoro-n-alkanesulfonates) of the formula I and their use as precursors for the preparation of chiral phosphine ligands for transition metal catalysts.

Chiral phosphine ligands such as 2,2'-bis (diphenylphosphino)-1,1'-binaphthyl (BINAP) and analogous phosphines are of great importance as constituents of transition metal catalysts used in enantioselective hydrogenations or CC couplings. Various ways of preparing these phosphines are known in the literature. In general, these start from the corresponding binaphthols or analogous phenol derivatives whose hydroxy groups are converted into leaving groups and subsequently replaced by phosphine groups.

U.S. Pat. No. 5,399,771 discloses a process for preparing BINAP starting from enantiomerically pure binaphthol which is firstly converted into the corresponding bis (trifluoromethanesulfonate). BINAP is subsequently obtained by nickel-catalysed coupling with diphenylphosphine. Disadvantages of this process are the high price and the difficulty of industrial handling of the sensitive and extremely aggressive trifluoromethanesulfonic anhydride in the preparation of binaphthol bis (trifluoromethanesulfonate). The use of other trifluoromethanesulfonic acid derivatives such as trifluoromethanesulfonyl fluoride or chloride is also difficult in process engineering terms due to the high volatility of the compounds (b.p.=−20° C. and 32° C., respectively).

It is an object of the invention to provide a process which can be carried out industrially, does not have the abovementioned disadvantages and makes it possible to obtain, inexpensively and technically simply, compounds which are suitable as starting substances for the synthesis of chiral and phosphine ligands for transition metal catalysts.

It has surprisingly been found that the compounds of the formula I can be obtained in a simple manner by reacting the respective phenols with the corresponding perfluoro-n-alkanesulfonyl fluorides, chlorides or anhydrides and that significantly improved yields in the preparation of phosphine ligands for transition metal catalysts are obtained by use of the compounds of the formula I.

The corresponding relatively long-chain perfluoroalkanesulfonyl fluorides, chlorides or anhydrides are commercially available at favourable prices or can easily be prepared by known methods (e.g. DE 1912738, DE 42118562).

The invention accordingly provides bis(perfluoro-n-alkanesulfonates) of the formula I:

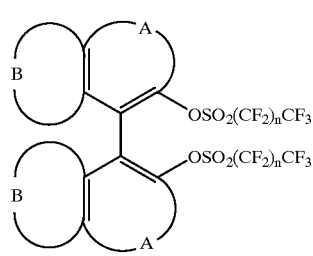

where

A, B and n are as defined above.

The invention further provides a process for preparing the bis(perfluoro-n-alkanesulfonates) of the formula I, characterized in that compounds of the formula II

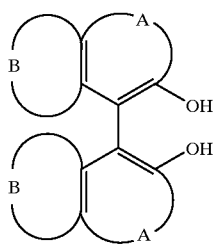

where A and B are as defined above are reacted with the corresponding perfluoro-n-alkanesulfonyl fluoride, chloride or anhydride in the presence of a base.

The bis(perfluoro-n-alkanesulfonates) of the formula I prepared from the phenols of the formula II by the process of the invention are, in particular, valuable intermediates for the synthesis of chiral catalysts such as 2,2′-bis(diphenylphosphino)-1,1′-binaphthyl (BINAP) and analogous compounds.

A is preferably

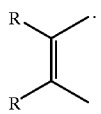

B is preferably —$(CHR_2)_4$— or

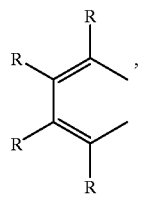

in particular

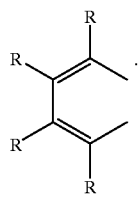

n is preferably 3, 4, 5 or 7, in particular 3 or 7. n is very particularly preferably 3. R is preferably alkyl or alkoxy having from 1 to 7 carbon atoms, F, Br, CN, —$CF_3$, —$OCF_3$, in particular —$CH_3$, —$OCH_3$, CN or —$CF_3$.

If R in the formulae above and below is an alkyl radical or an alkoxy radical, this may be linear or branched. It is preferably linear and has 1, 2, 3, 4, 5, 6 or 7 carbon atoms, and is thus preferably methyl, ethyl, propyl, butyl, pentyl, hexyl, heptyl, methoxy, ethoxy, propoxy, butoxy, pentyloxy, hexyloxy or heptyloxy, also octyl, nonyl, decyl, undecyl, dodecyl, tridecyl, tetradecyl, pentadecyl, octyloxy, nonyloxy, decyloxy, undecyloxy, dodecyloxy, tridecyloxy or tetradecyloxy.

The radical R can also be an optically active organic radical having an asymmetric carbon atom.

Above and below, halogen is fluorine, chlorine, bromine or iodine, preferably fluorine, chlorine or bromine. Halogen is particularly preferably fluorine or bromine.

Perfluoro-n-alkanesulfonates of the component formulae I1–I13 are particularly preferred embodiments of the invention.

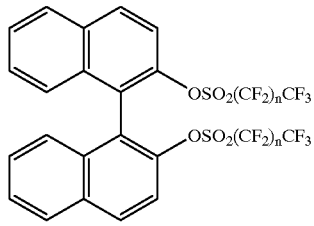

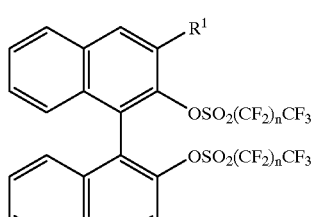

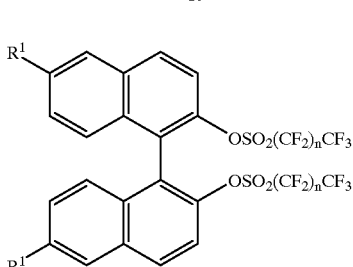

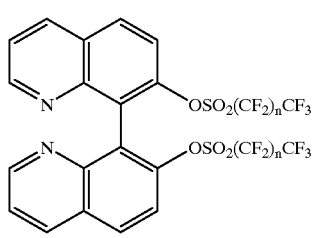

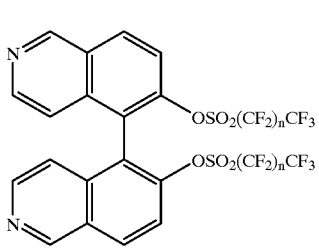

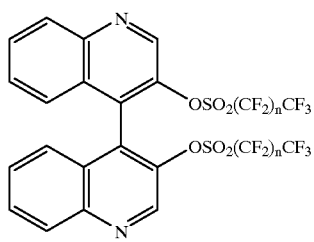

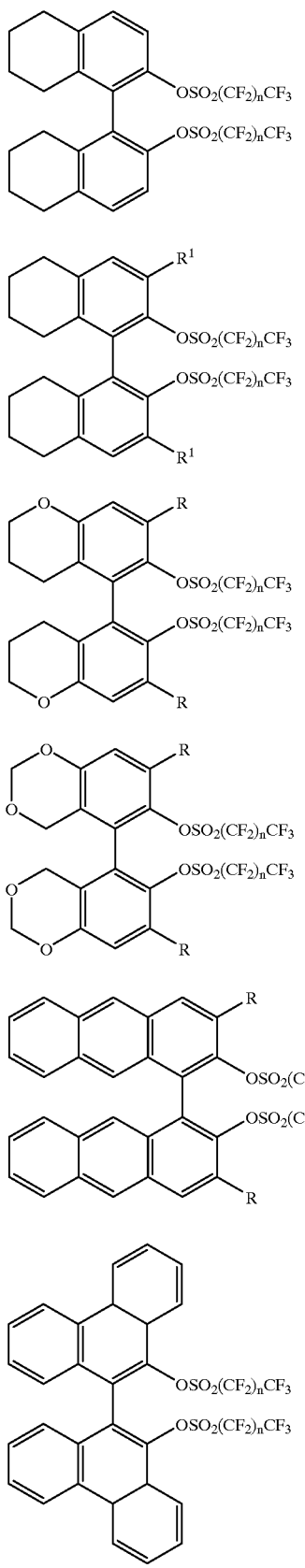

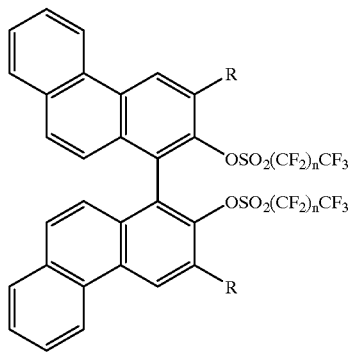

where R and n are as defined above and $R^1$ is alkyl or alkoxy having from 1 to 3 carbon atoms, F, Br, $CF_3$ or CN.

Very particular preference is given to the compounds of the formulae I1, I2, I3, I7 and I8.

The reaction procedure of the process of the invention for preparing the compounds of the formula I is simple, with the corresponding phenol derivative of the formula II being reacted with the corresponding perfluoro-n-alkanesulfonyl fluoride, chloride or anhydride at temperatures of from −30° C. to +70° C., preferably from −10° C. to +50° C., in particular from 0 to 30° C., under superatmospheric or subatmospheric pressure, preferably at atmospheric pressure, in the presence of a base. Preference is given to using perfluoro-n-alkanesulfonyl fluoride to obtain the perfluoro-n-alkanesulfonates of the formula I. As perfluoro-n-alkanesulfonyl fluorides, preference is given to using nonafluoro-n-butanesulfonyl fluoride or perfluoro-n-octanesulfonyl fluoride. Very particular preference is given to nonafluoro-n-butanesulfonyl fluoride.

The molar ratio of the respective phenol of the formula II to perfluoro-n-alkanesulfonyl fluoride, chloride or anhydride is, in the process of the invention, generally from 1:2 to 1:20, preferably from 1:2 to 1:10. A ratio of from 1:2 to 1:5 is particularly preferred.

The reaction can be carried out in the presence of equimolar amounts of base and perfluoro-n-alkanesulfonyl fluoride, chloride or anhydride or using an excess of the respective base.

Suitable bases for the process of the invention for preparing the compounds of the formula I are, for example, alkali metal carbonates and alkaline earth metal carbonates, for example sodium, potassium, magnesium or calcium carbonate. Particularly suitable bases are nitrogen heterocycles, amines or amidines. Preference is given to using nitrogen bases in which no H atoms are directly bound to an N atom. Preferred nitrogen bases are pyridines, pyrimidines, pyridazines, trialkylamines and dialkylarylamines, where the alkyl radicals in the trialkylamines and dialkylarylamines can be identical or different. Particular preference is given to imidazole, pyridine, p-dimethylaminopyridine, m-dimethylaminopyridine, o-dimethylaminopyridine, pyrimidine, trimethylamine, triethylamine, tripropylamine, triisopropylamine, dimethylaniline, diethylaniline. Very particular preference is given to pyridine, imidazole, p-dimethylaminopyridine, m-dimethylaminopyridine, trimethylamine, triethylamine and dimethylaniline. It is also possible to use mixtures of the nitrogen bases mentioned.

The reaction time is generally from 0.1 to 24 hours, preferably from 0.2 to 6 hours.

The reaction of the phenol with perfluoro-n-alkanesulfonyl fluoride, chloride or anhydride can be carried out in the melt or in solvents. Preference is given to carrying out the reaction in the presence of organic solvents.

Suitable solvents for the process for preparing the compounds of the formula I are halogenated hydrocarbons such as dichloromethane, trichloromethane, dichloroethylene or trichloroethylene, amides such as N,N-dimethylformamide or N-methylpyrrolidone or aromatic hydrocarbons such as benzene, toluene, xylenes, mesitylene, anisole, phenetole or tetrahydronaphthalene. It is also possible to use saturated hydrocarbons such as cyclohexane, n-hexane or n-octane, esters such as methyl acetate, ethyl acetate, propyl acetate or butyl acetate or ethers such as diethyl ether, methyl tert-butyl ether, tetrahydrofuran or dioxane. Preferred solvents for the process of the invention are dichloromethane, trichloromethane, dichloroethylene or trichloroethylene, N,N-dimethylformamide, N-methylpyrrolidone, benzene, toluene, in particular dichloromethane, trichloromethane, dichloroethylene or trichloroethylene.

Mixtures of the abovementioned solvents can likewise be used. It is likewise possible to use the abovementioned bases as solvents.

The amount of solvent is not critical; in general, from 10 to 10,000 g of solvent can be added per mole of phenol of the formula II to be reacted.

In general, essentially water-free solvents should be used.

Only when using appropriately large amounts of perfluoro-n-alkanesulfonyl fluoride, chloride or anhydride and the respective base can water present in the reaction mixture be neglected.

The compounds of the formula I can be obtained, for example, according to the following scheme:

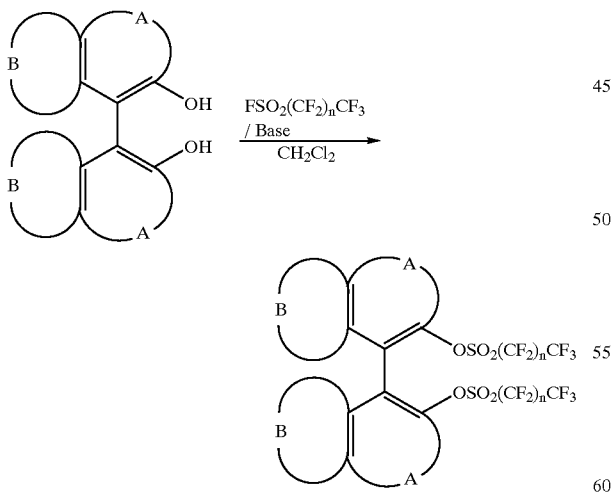

where A, B and n are as defined above.

The invention further provides for the use of the bis (perfluoro-n-alkanesulfonates) of the formula I as precursors for preparing chiral phosphine compounds of the formula III

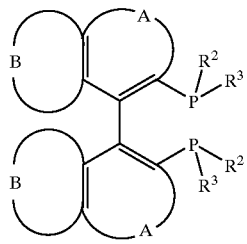

where A and B are as defined-above and $R^2, R^3$ are, independently of one another, phenyl, 4-methylphenyl, 3-methylphenyl, 2-methylphenyl, 3,5-dimethylphenyl, 3,5-di-tert-butylphenyl, 4-methoxyphenyl, 3-methoxyphenyl, 2-methoxyphenyl, 3,5-dimethoxyphenyl, cyclohexyl or cyclopentyl, and also provides a process for preparing the compounds of the formula III, characterized in that the compounds of the formula I are reacted in the presence of a transition metal catalyst and a base either with phosphines of the formula IV $$H\text{—}P\begin{smallmatrix}R^2\\R^3\end{smallmatrix} \qquad IV$$

or with zinc and phosphines of the formula V $$Cl\text{—}P\begin{smallmatrix}R^2\\R^3\end{smallmatrix} \qquad V$$

where $R^2$ and $R^3$ are as defined above.

The compounds of the formula III are used, in particular, as chiral ligands for transition metal catalysts which make it possible to carry out enantioselective reactions such as hydrogenations or C,C couplings.

The preferred meanings of the groups A and B given for the compounds of the formula I also apply to the compounds of the formulae II and III.

$R^2$ and $R^3$ are preferably, independently of one another, phenyl, 4-methylphenyl, 3-methylphenyl, 3,5-dimethylphenyl, 3,5-di-tert-butylphenyl or cyclohexyl. $R^2$ and $R^3$ are particularly preferably phenyl. Compounds of the formula III in which $R^2$ and $R^3$ have the same meaning are very particularly preferred.

Particularly preferred compounds of the formula III which can be prepared using the compounds of the formula I are those of the component formulae III1–III16:

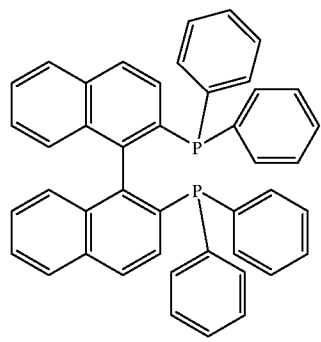
III1
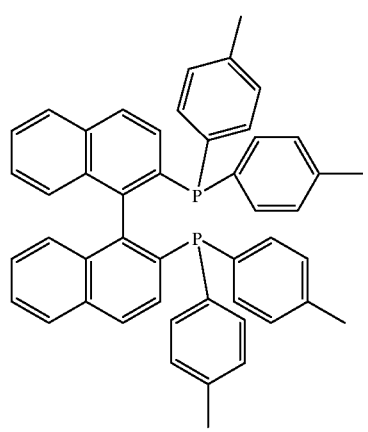
III2
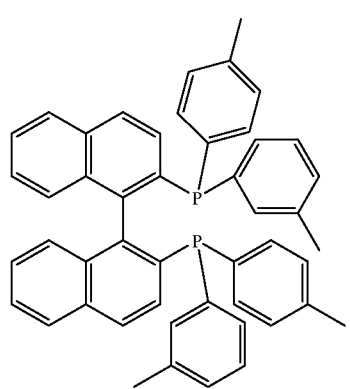
III3
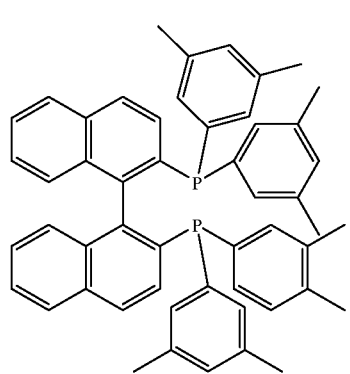
III4
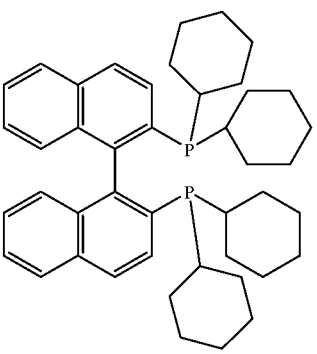
III5
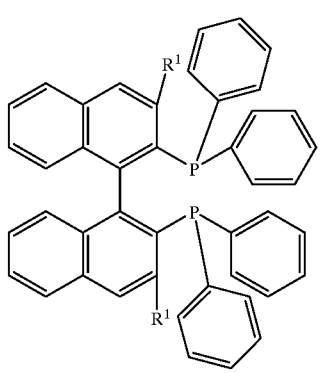
III6
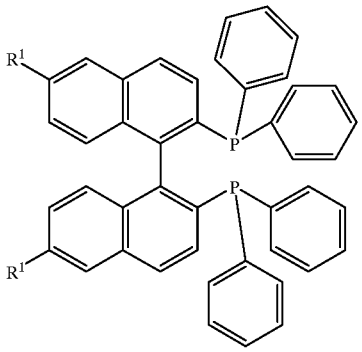
III7
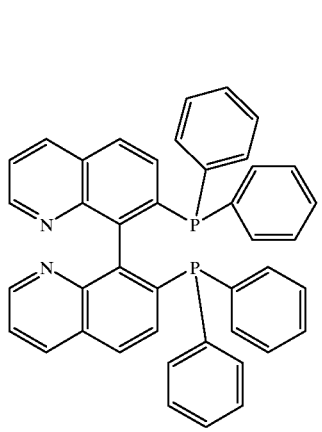
III8

III9
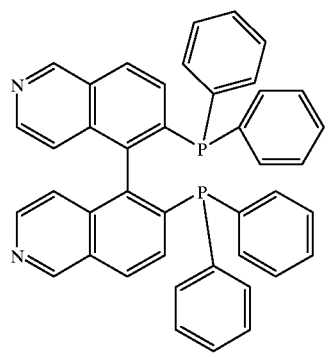
III10
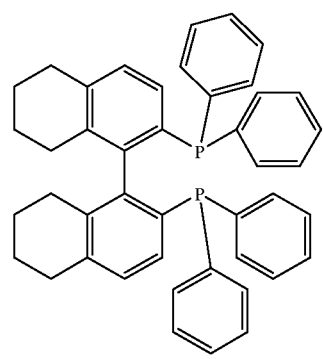
III11
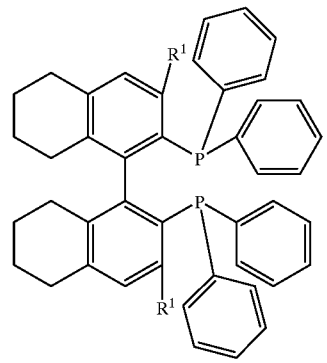
III12
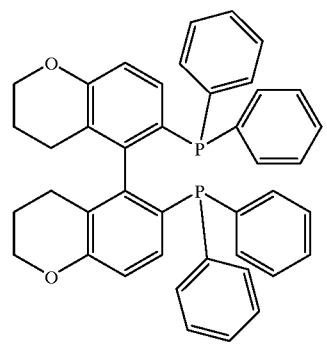
III13
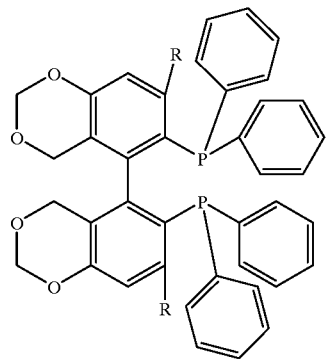
III14
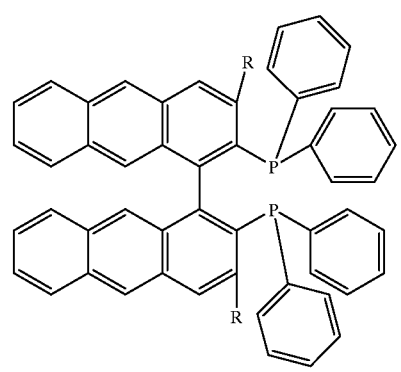
III15
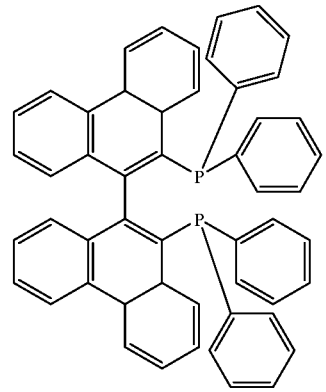
III16
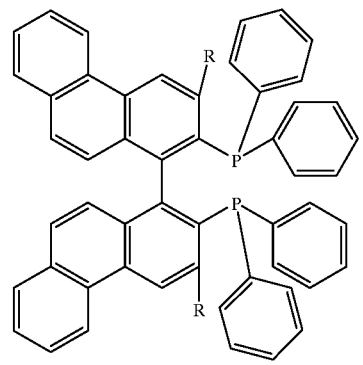
where R and R$^1$ are as defined above.

The compounds of the formula III can be prepared by reacting the perfluoro-n-alkanesulfonates of the formula I, preferably in an organic solvent, with a phosphine of the formula IV at temperatures of from 20° C. to 150° C., preferably 30°–120° C., in particular from 40° to +100° C., under superatmospheric or subatmospheric pressure, preferably at atmospheric pressure, in the presence of a base and a transition metal catalyst.

The compounds of the formula III can also be prepared by reacting the perfluoro-n-alkanesulfonates of the formula I, preferably in the absence of solvent, with a phosphine of the formula V at temperatures of from 20° C. to 150° C., preferably 30°–120° C., in particular from 40° to +100° C., at superatmospheric or subatmospheric pressure, preferably at atmospheric pressure, in the presence of a base, zinc and a transition metal catalyst.

Zinc is preferably used in the form of a fine powder. The molar ratio of the respective perfluoro-n-alkanesulfonate of the formula I to zinc used is generally from 1:2 to 1:40, preferably from 1:2 to 1:20, in the process of the invention for preparing the compounds of the formula III. Particular preference is given to a ratio of from 1:2 to 1:10.

The molar ratio of the respective perfluoro-n-alkanesulfonate of the formula I to the phosphines of the formula IV or V is generally from 1:2 to 1:20, preferably from 1:2 to 1:10, in the process of the invention for preparing the compounds of the formula III. Particular preference is given to a ratio of from 1:2 to 1:5.

The molar ratio of the respective perfluoro-n-alkanesulfonate of the formula I to the base used is generally from 1:2 to 1:20, preferably from 1:2 to 1:15. Particular preference is given to a ratio of from 1:2 to 1:10.

The molar ratio of the respective perfluoro-n-alkanesulfonate of the formula I to the transition metal catalyst used is generally from 100:1 to 2:1, preferably from 50:1 to 5:1. Particular preference is given to a ratio of from 20:1 to 10:1.

As transition catalysts for the conversion of the compounds of the formula I into the phosphines of the formula III, preference is given to using nickel and palladium catalysts such as palladium acetate, $PdCl_2$, $PdCl_2$-bis(triphenylphosphine) or Pd-tetrakis(triphenylphosphine). Nickel catalysts are preferably used. Particular preference is given to $NiCl_2$-bis(diphenyl)phosphinylmethane, -ethane, -propane or -butane, $NiBr_2$, $NiCl_2$, $NiCl_2$-bis(diphenyl)phosphinylferrocene, $NiCl_2$-bis(triphenylphosphine), Ni-tetrakis(triphenylphosphine), Ni-tetrakis(triphenyl phosphite) or Ni-dicarbonylbis(triphenylphosphine). Very particular preference is given to $NiCl_2$, $NiCl_2$-bis(diphenyl)phosphinylethane or $NiCl_2$-bis(diphenyl)phosphinylpropane. The catalysts can also be formed in situ by adding the transition metal or transition metal salt and the corresponding ligand separately to the reaction mixture. It is likewise possible to add mixtures of transitional metal catalysts to the reaction mixture.

Suitable bases for the conversion of the compounds of the formula I into the phosphines of the formula III are, for example, alkali metal carbonates and alkaline earth metal carbonates, for example sodium, potassium, magnesium or calcium carbonate. Particularly suitable bases are nitrogen heterocycles, amines or amidines. Preference is given to using nitrogen bases in which no H atoms are bound directly to an N atom. Preferred nitrogen bases are pyridines, pyrimidines, pyridazines, trialkylamines, dialkylarylamines or DABCO (diazabicyclo[2.2.2]octane), where the alkyl radicals in the trialkylamines and dialkylarylamines can be identical or different. Particular preference is given to DABCO, imidazole, pyridine, p-dimethylaminopyridine, m-dimethylaminopyridine, o-dimethylaminopyridine, pyrimidine, trimethylamine, triethylamine, tripropylamine, triisopropylamine, dimethylaniline, diethylaniline.

Very particular preference is given to DABCO, pyridine, imidazole, p-dimethylaminopyridine, m-dimethylaminopyridine, trimethylamine, triethylamine and dimethylaniline. It is also possible to use mixtures of the nitrogen bases mentioned.

The reaction time is generally from 1 hour to 6 days.

Preference is given to using polar solvents for the conversion of the compounds of the formula I into the phosphines of the formula III. Suitable solvents are, for example, amides such as N,N-dimethylformamide or N-methylpyrrolidone, sulfolane, sulfoxides such as dimethyl, diethyl or dibutyl sulfoxide, nitriles such as acetonitrile or propionitrile, esters such as methyl acetate or ethyl acetate or ethers such as tetrahydrofuran or dioxane or ketones such as acetone. Preferred solvents for the process of the invention are N,N-dimethylformamide, N-methylpyrrolidone, sulfolane, dimethyl sulfoxide or acetonitrile. Mixtures of the solvents mentioned can likewise be used. It is likewise possible to use the abovementioned nitrogen bases as solvents.

The amount of solvent is not critical; in general, from 10 to 10,000 g of solvent can be added per mole of perfluoro-n-alkanesulfonate to be reacted.

The compounds of the formula III can be obtained, for example, according to the following scheme:

Scheme 2

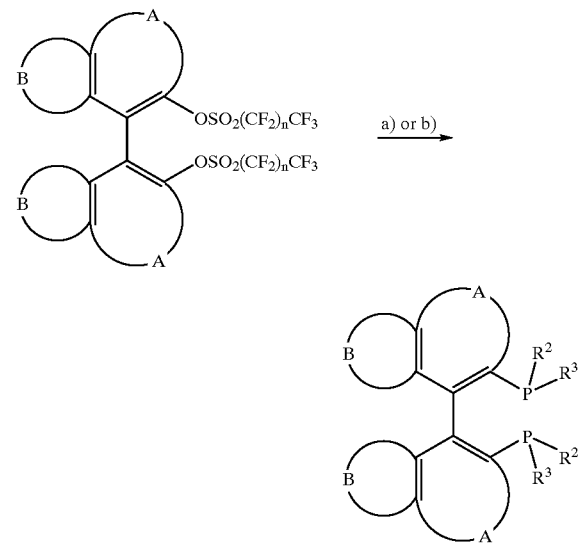

a) $HPR^2R^3$, base, $NiCl_2$dppe
b) $ClPR^2R^3$, Zn, base, $NiCl_2$,
where A, B, n and $R^2$ and $R^3$ are as defined above.

The formulae I, II and III include both the R and the S enantiomers of the compounds. Likewise, the mixtures of the enantiomers are encompassed by these formulae.

The compounds of the formulae II, IV and V required as starting materials are either known or can be prepared by methods known per se, as are described in the literature (e.g. in standard works such as Houben-Weyl, Methoden der Organischen Chemie, Georg-Thieme-Verlag, Stuttgart), under reaction conditions which are known and suitable for the specified reactions. Use can also be made here of variants which are known per se but are not described in more detail here.

Even without further embodiments, it is assumed that a person skilled in the art will be able to make very wide use of the above description. The preferred embodiments are therefore to be regarded merely as a descriptive, but in no way limiting, disclosure.

The following examples illustrate the invention, without limiting it. Percentages mentioned above and below are by weight. All temperatures are reported in degrees Celsius. The expression "room temperature" refers to 20° C.

EXAMPLE 1

Racemic Binaphthol Dinonaflate(binaphthol Bis(nonafluoro-n-butanesulfonate))

111.6 g of nonafluoro-n-butanesulfonyl fluoride (370 mmol) were added at room temperature to a solution of 45.6 g of racemic binaphthol (160 mmol) and 47.6 g of triethylamine (470 mmol; 65.5 ml) in 350 ml of dichloromethane. After a few minutes, the denser sulfonyl phase had disappeared, without the mixture warming appreciably. After stirring for 4 hours, the mixture was shaken once with 80 ml of aqueous sodium hydroxide solution (5% by weight) and once with 80 ml of water, and the organic phase was dried over sodium sulfate and concentrated on a rotary evaporator. The product crystallized out on cooling and was purified further by washing with a small amount of cold methanol and subsequent filtration with suction. This gave 123 g of binaphthol dinonaflate (90.0%) as colourless crystals having a melting point of 104.1° C.; HPLC purity>99% (RP-18; methanol/water 80:20; 254 nm).

EXAMPLE 2

(R)- or (S)-binaphthol Dinonaflate

The preparation of (R)- or (S)-binaphthol dinonaflate was carried out by the method indicated for the corresponding racemate using (R)- or (S)-binaphthol, which is, for example, obtainable as described in U.S. Pat. No. 5,399,771. The only difference is the honey-like consistency of the pure enantiomers of binaphthol dinonaflate which, combined with a much higher solubility in methanol, makes purification by washing with this solvent impossible. The product obtained amounted to 95% of theory of a high-viscosity liquid which gradually crystallized after standing for a number of weeks at room temperature (HPLC purity>98%; RP-18; methanol/water 80:20). The enantiomeric purity was determined by means of HPLC and corresponded exactly to that of the binaphthol used (Chiradex 10 μm; solution in methanol; c=1 mg/ml; $CH_3OH/H_2O$ 70:30; 254 nm). $[\alpha]^D = -87.4°$ ((R)-binaphthol dinonaflate; c=1 THF; 20° C.).

The following novel compounds were obtained analogously from the appropriate precursors:

EXAMPLES 3–15

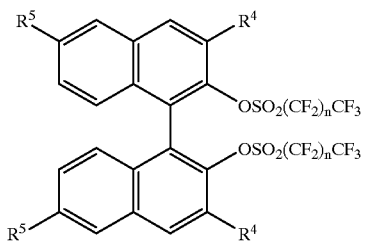

|      | n | $R^4$    | $R^5$    |
|------|---|----------|----------|
| (3)  | 3 | methyl   | H        |
| (4)  | 3 | ethyl    | H        |
| (5)  | 3 | methoxy  | H        |
| (6)  | 3 | $CF_3$   | H        |
| (7)  | 7 | CN       | H        |
| (8)  | 7 | phenyl   | H        |
| (9)  | 3 | F        | methyl   |
| (10) | 3 | CN       | methoxy  |
| (11) | 4 | H        | methyl   |
| (12) | 5 | H        | pentyl   |
| (13) | 7 | H        | methoxy  |
| (14) | 3 | H        | CN       |
| (15) | 3 | H        | phenyl   |

EXAMPLES 16–23

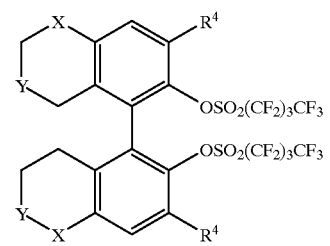

|      | $R^4$   | X      | Y      |
|------|---------|--------|--------|
| (16) | H       | $CH_2$ | $CH_2$ |
| (17) | CN      | $CH_2$ | $CH_2$ |
| (18) | $CF_3$  | $CH_2$ | $CH_2$ |
| (19) | methoxy | $CH_2$ | $CH_2$ |
| (20) | H       | O      | $CH_2$ |
| (21) | CN      | O      | $CH_2$ |
| (22) | methyl  | O      | O      |
| (23) | $CF_3$  | O      | O      |

EXAMPLES 24–26

(24)
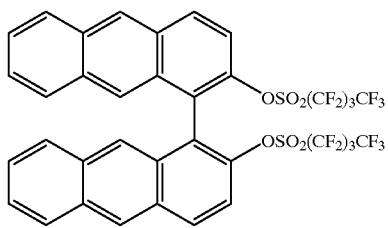

(25)
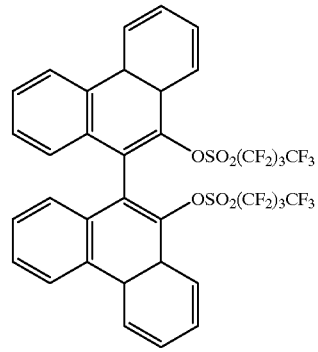

(26)
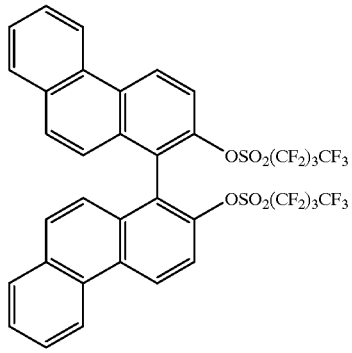

EXAMPLE 27

1.25 ml of diphenylphosphine were added at room temperature and under argon to a suspension of 663 mg of NiCl$_2$(dppe) in 25 ml of DMF. After stirring for half an hour at 100° C., a solution of 5.63 g of DABCO and 10.6 g of enantiomerically pure (R)- or (S)-binaphthol dinonaflate or racemic binaphthol dinonaflate (125 mmol) in 37.5 ml of DMF was added in a countercurrent of argon by means of a syringe fitted with an injection needle. The reaction mixture was maintained at 100° C.; after one, three and seven hours, 1.25 ml in each case of diphenylphosphine were added. The progress of the reaction was followed by HPLC (Purospher RP-18; acetonitrile/water 90:10). After all the starting material had been consumed (about two days; the reaction can be accelerated by occasional addition of, in each case, 0.15 g of DABCO and 50 mg of NiCl$_2$(dppe)), the reaction mixture was allowed to cool. Filtration with suction and washing with a little cold methanol gave (R)-, (S)- or racemic 2,2'-bis(diphenylphosphine)-1,1'-binaphthyl (BINAP) as a snow white, finely crystalline powder in a yield of 77% (8.1 g; 125 mmol).

EXAMPLE 28

A reaction mixture of 400 mg of zinc dust, 300 mg of DABCO, 25 mg of nickel(II) chloride, 1.0 g of racemic or enantiomerically pure binaphthol dinonaflate and 0.30 ml of chlorodiphenylphosphine was heated to 100° C. under protective gas. The progress of the reaction was followed by HPLC monitoring; every three hours, a further 25 mg of NiCl$_2$ and, if necessary, also chlorodiphenylphosphine were added. After all the starting material had been consumed, the reaction mixture was allowed to cool. The precipitate was filtered off with suction and boiled with toluene. Filtration under protective gas and cooling to 5° C. gave (R)-, (S)- or racemic BINAP as a snow white, finely crystalline powder.

The following compounds were obtained analogously from the appropriate precursors:

EXAMPLES 29–41

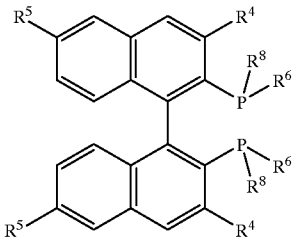

|      | $R^6$          | $R^4$     | $R_5$    |
|------|----------------|-----------|----------|
| (29) | phenyl         | methyl    | H        |
| (30) | 4-methylphenyl | ethyl     | H        |
| (31) | phenyl         | methoxy   | H        |
| (32) | phenyl         | CF$_3$    | H        |
| (33) | phenyl         | CN        | H        |
| (34) | phenyl         | phenyl    | H        |
| (35) | cyclohexyl     | F         | methyl   |
| (36) | 3-methylphenyl | CN        | methoxy  |
| (37) | phenyl         | H         | methyl   |
| (38) | 4-methylphenyl | H         | pentyl   |
| (39) | cyclohexyl     | H         | methoxy  |
| (40) | phenyl         | H         | CN       |
| (41) | phenyl         | H         | phenyl   |

EXAMPLES 42–49

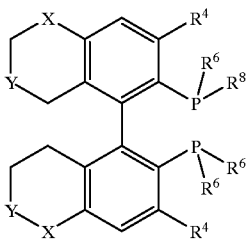

|      | $R^6$  | $R^4$   | X       | Y       |
|------|--------|---------|---------|---------|
| (42) | phenyl | H       | CH$_2$  | CH$_2$  |
| (43) | phenyl | CN      | CH$_2$  | CH$_2$  |
| (44) | phenyl | CF$_3$  | CH$_2$  | CH$_2$  |

-continued

| | R⁶ | R⁴ | X | Y |
|---|---|---|---|---|
| (45) | 4-methylphenyl | methoxy | $CH_2$ | $CH_2$ |
| (46) | 3-methylphenyl | H | O | $CH_2$ |
| (47) | cyclohexyl | CN | O | $CH_2$ |
| (48) | cyclopentyl | methyl | O | O |
| (49) | phenyl | $CF_3$ | O | O |

EXAMPLES 50–52

(50)

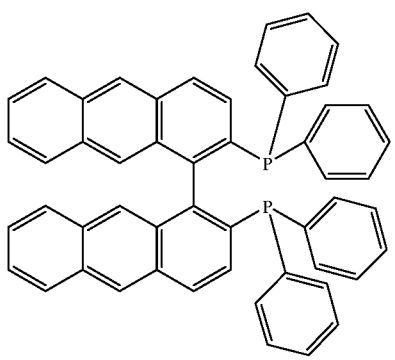

(51)

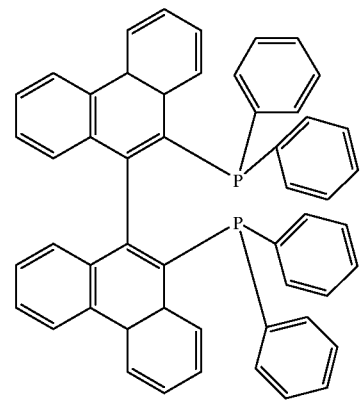

(52)

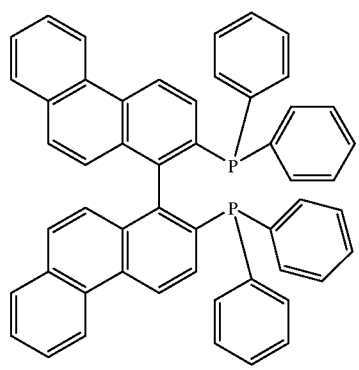

What is claimed is:

1. A bis(perfluoro-n-alkanesulfonate) compound of the formula I:

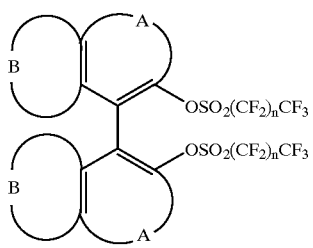

where
n is 3, 4, 5, 6, 7, 8 or 9,

A is 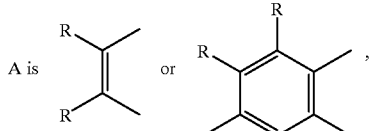

B is —$(CHR)_4$—, 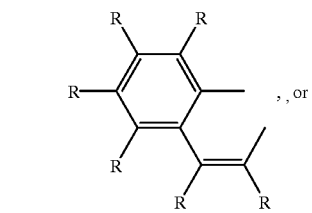

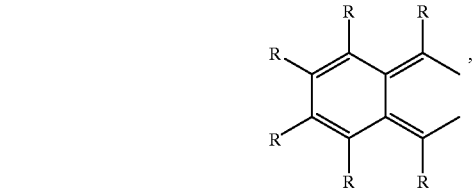

where
R is alkyl or alkoxy having from 1 to 12 carbon atoms, halogen, —CN, —$CF_3$, —$OCF_3$ or unsubstituted phenyl or phenyl which is monosubstituted or polysubstituted by alkyl or alkoxy having from 1 to 12 carbon atoms, halogen or —CN, where if more than one R is present the substituents R may be identical or different.

2. A compound of the formula I according to claim 1, wherein A is

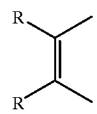

and B is —$(CHR_2)_4$— or

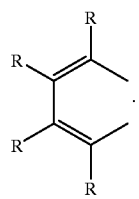

3. A compound of the formula I according to claim 1, wherein R is alkyl or alkoxy having from 1 to 7 carbon atoms, F, Br, CN, —$CF_3$, —$OCF_3$.

4. A compound of claim 1 which is of the formulae I1, I2, I3, I7 or I8:

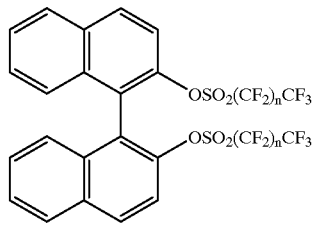

I1

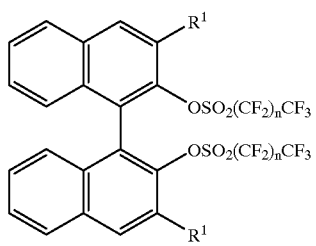

I2

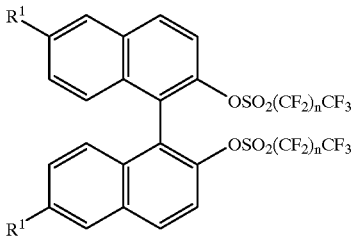

I3

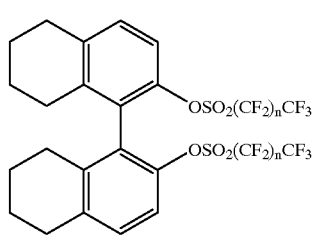

I7

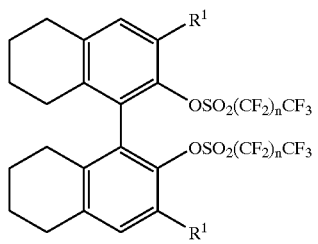

I8 where n is as defined above and $R^1$ is alkyl or alkoxy having from 1 to 3 carbon atoms, F, Br, $CF_3$ or CN.

5. A process for preparing a compound of claim 1, which comprises reacting a compound of the formula II:

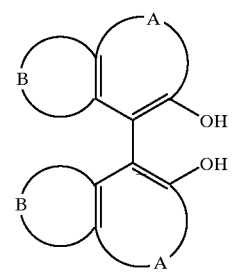

II where A and B are as defined with a perfluoro-n-alkanesulfonyl fluoride, chloride or anhydride in the presence of a base.

6. The process of claim 5, wherein the compounds of the formula II are reacted with nonafluoro-n-butanesulfonyl fluoride or perfluoro-n-octanesulfonyl fluoride in the presence of a base.

7. The process of claim 5, wherein the base used is a pyridine, a pyrimidine, a pyridazine, a trialkylamine or a dialkylarylamine.

8. A method for preparing a diphosphine of formula III using a bis(perfluoro-n-alkanesulfonate) compound of the formula I of claim 1, which comprises reacting a compound of the formula I, in the presence of a transition metal catalyst and a base, with either a phosphine of the formula IV or zinc and a phosphine of the formula V:

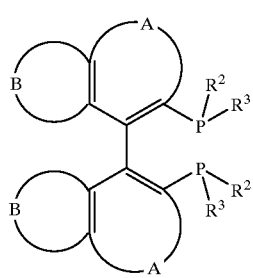

III where A and B are as defined above and
$R^2$, $R^3$ are phenyl, 4-methylphenyl, 3-methylphenyl, 2-methylphenyl, 3,5-dimethylphenyl, 3,5-ditertbutylphenyl, 4-methoxyphenyl, 3-methoxyphenyl, 2-methoxyphenyl, 3,5-dimethoxyphenyl, cyclohexyl or cyclopentyl;

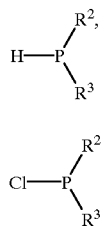

where $R^2$ and $R^3$ are as defined above.

9. A process according to claim 8, wherein the transition metal catalyst used is a nickel catalyst.

10. The process of claim 5, wherein the reaction is conducted at a temperature of –30° C. to +70 ° C.

11. The process of claim 5, wherein the molar ratio of the compound of formula II to the perfluoro-n-alkanesulfonyl fluoride, chloride or anhydride is from 1:2 to 1:20.

12. The method of claim 8, wherein $R^2$ and $R^3$ are both phenyl.

13. The method of claim 8, wherein the reaction is conducted at a temperature from 20° C. to 150° C.

14. The method of claim 8, wherein the compound of formula I is reacted with zinc and a phosphine of the formula V and the molar ratio of the compound of the formula I to the zinc is from 1:2 to 1:40.

15. The method of claim 8, wherein the molar ratio of the compound of the formula I to the phosphine of formula IV or phosphine of formula V is from 1:2 to 1:20.

16. The method of claim 8, wherein the molar ratio of the compound of the formula I to the base is from 1:2 to 1:20.

17. The method of claim 8, wherein the molar ratio of the compound of the formula I to the transition metal catalyst is from 100:1 to 2:1.

* * * * *